(12) United States Patent
Kobayashi

(10) Patent No.: US 12,023,100 B2
(45) Date of Patent: Jul. 2, 2024

(54) EYEBALL IMAGING DEVICE AND DIAGNOSIS SUPPORT SYSTEM

(71) Applicant: Yoichiro Kobayashi, Okayama (JP)

(72) Inventor: Yoichiro Kobayashi, Okayama (JP)

( * ) Notice: Subject to any disclaimer, the term of this patent is extended or adjusted under 35 U.S.C. 154(b) by 353 days.

(21) Appl. No.: 17/631,530

(22) PCT Filed: Jul. 28, 2020

(86) PCT No.: PCT/JP2020/028881
§ 371 (c)(1),
(2) Date: Jul. 18, 2022

(87) PCT Pub. No.: WO2021/020388
PCT Pub. Date: Feb. 4, 2021

(65) Prior Publication Data
US 2022/0338732 A1 Oct. 27, 2022

(30) Foreign Application Priority Data
Jul. 31, 2019 (JP) .................................. 2019-141530

(51) Int. Cl.
*A61B 3/14* (2006.01)
*A61B 3/00* (2006.01)
*H04N 23/90* (2023.01)

(52) U.S. Cl.
CPC ............ *A61B 3/145* (2013.01); *A61B 3/0083* (2013.01); *H04N 23/90* (2023.01)

(58) Field of Classification Search
None
See application file for complete search history.

(56) References Cited

U.S. PATENT DOCUMENTS

2005/0270484 A1* 12/2005 Maeda ............... A61B 3/185
351/206
2007/0146636 A1* 6/2007 Ishikura ............. A61B 3/152
351/221

(Continued)

FOREIGN PATENT DOCUMENTS

CA 3037258 A1 * 3/2018 ........... A61B 3/0008
CN 103654708 A * 3/2014 ........... A61B 3/0008

(Continued)

OTHER PUBLICATIONS

English translation of Written Opinion of the International Searching Authority issued on Sep. 15, 2020 for corresponding International Patent Application No. PCT/JP2020/028881.

(Continued)

*Primary Examiner* — Ricky Chin
(74) *Attorney, Agent, or Firm* — Hauptman Ham, LLP

(57) ABSTRACT

An eye imaging device including a housing with an opening that can be in contact with a head of an observer, a first photographic optical system arranged in the housing and configured to image a left eyeball of the observer from a side, a second photographic optical system arranged in the housing opposite to the first photographic optical system and configured to image a right eyeball of the observer from a side, a third photographic optical system arranged slidable in the housing in a direction in which the first photographic optical system and the second photographic optical system face each other and configured to image the left eyeball and the right eyeball of the observer from a front, and a storage unit configured to store images captured by the first photographic optical system, the second photographic optical system, and the third photographic optical system is provided.

12 Claims, 9 Drawing Sheets

(56) References Cited

U.S. PATENT DOCUMENTS

| | | | | |
|---|---|---|---|---|
| 2013/0135586 A1* | 5/2013 | Lai | ............... | A61B 3/1015 |
| | | | | 351/216 |
| 2013/0222764 A1* | 8/2013 | Thompson | ............... | A61B 3/18 |
| | | | | 351/209 |
| 2019/0041643 A1* | 2/2019 | Chang | ............... | H04N 13/398 |
| 2019/0110679 A1* | 4/2019 | Mackool | ............... | A61B 3/032 |
| 2022/0338732 A1* | 10/2022 | Kobayashi | ............... | A61B 3/10 |

FOREIGN PATENT DOCUMENTS

| | | | | | |
|---|---|---|---|---|---|
| EP | 1426006 A1 * | 6/2004 | | ............ | A61B 3/032 |
| EP | 3692891 A1 * | 8/2020 | | ............ | A61B 3/111 |
| JP | 2002-10978 A | 1/2002 | | | |
| JP | 2004-81387 A | 3/2004 | | | |
| JP | 2008-284273 A | 11/2008 | | | |
| JP | 2019-68932 A | 5/2019 | | | |
| WO | WO-2010117386 A1 * | 10/2010 | | ............ | A61B 3/032 |
| WO | WO-2015003086 A1 * | 1/2015 | | ........... | A61B 3/0025 |
| WO | WO-2017019771 A1 * | 2/2017 | | ........... | A61B 3/0025 |
| WO | WO-2020116669 A1 * | 6/2020 | | ............ | A61B 3/005 |
| WO | WO-2020209401 A1 * | 10/2020 | | ............ | A61B 3/145 |

OTHER PUBLICATIONS

International Search Report issued for corresponding International Patent Application No. PCT/JP2020/028881 on Sep. 15, 2020, along with an English translation.
Written Opinion issued for corresponding International Patent Application No. PCT/JP2020/028881 on Sep. 15, 2020.

* cited by examiner

FIG. 5

| 1 | Medical interview |
|---|---|
| 2 | Anterior segment of the eye examination |
| 3 | Measurement of the radius of curvature of the cornea |
| 4 | Measurement of the diameter of the cornea |
| 5 | Measurement of the naked eye visual acuity |
| 6 | Refraction test |
| 7 | Tear fluid volume test |
| 8 | Select trial lens |
| 9 | Wear the trial lens |
| 10 | Fitting inspection |
| 11 | Forced vision test |
| 12 | Determine the lens standard |
| 13 | Guidance on the appropriate handling |

EYEBALL IMAGING DEVICE AND DIAGNOSIS SUPPORT SYSTEM

CROSS-REFERENCE TO RELATED APPLICATIONS

The present application is a national stage filing under 35 U.S.C § 371 of PCT Application No. PCT/JP2020/028881 filed on Jul. 28, 2020, which is based on and claims priority to Japanese Patent Application No. 2019-141530 filed on Jul. 31, 2019, in the Japan Patent Office. The aforementioned applications are incorporated herein by reference in their entireties.

TECHNICAL FIELD

The present invention relates to an eye imaging device for imaging the eye of an observer. One embodiment of the present invention relates in particular to an eye imaging device that supports the prescription of contact lenses.

BACKGROUND ART

In recent years, the number of contact lens users has continued to increase, and it is estimated that there are already nearly 20 million contact lens users in Japan. With the increase in the number of contact lens users, the size of the contact lens market has been expanding and distribution patterns have been changing. Since contact lenses are not pharmaceutical products, they do not legally require a prescription from a medical institution to instruct the pharmacist. For this reason, contact lenses used to be sold only at ophthalmologists and contact lens specialty stores, but now, with the addition of sales at contact lens mass merchandisers, mail order sales, and Internet sales, they are becoming cheaper and easier to obtain.

On the other hand, under the Pharmaceutical Medical Devices Law, contact lenses are positioned as highly controlled medical devices with a high risk to the human body in the event of side effects or functional disorders. When a contact lens user receives a prescription for contact lenses at a conventional ophthalmologist or contact lens specialty store, the user first undergoes an examination by a medical specialist to check for abnormalities in the eyes. Then, the user select contact lenses and undergo a fitting inspection. In addition, the user can receive guidance on how to handle and properly care for the contact lenses. These proper examinations and guidance are necessary for the safe and comfortable use of contact lenses. However, in the case of sales at contact lens mass merchandisers, mail order sales, and Internet sales, it is not possible to receive such proper examinations and guidance, and there is a risk of eye problems caused by the use of contact lens due to various reasons.

Typical diseases caused by the use of contact lens include corneal erosion, corneal infection, corneal neovascularization, and giant papillary conjunctivitis, which can lead to blindness if left untreated. Although many contact lens users are aware of the importance of seeing an ophthalmologist, they still rely on mass merchandisers, mail-order sales, and Internet sales for contact lenses, which are cheaper and easier to purchase, due to the time constraints and financial burden of receiving examinations and guidance from medical specialists. For this reason, it is desirable to create an environment in which people can easily and inexpensively receive examinations and guidance from medical specialists at mass merchandisers, mail-order sales, and Internet sales of contact lenses.

For example, Patent Literature 1 discloses an ophthalmology remote diagnosis system with operability that enables an ophthalmologist to remotely operate an ophthalmology examination device to make a highly accurate diagnosis, even if the patient and the ophthalmology examination device are in a remote location.

CITATION LIST

Patent Literature

Patent Literature 1: Japanese Patent Publication No. 2008-284273

SUMMARY OF INVENTION

Technical Problem

Patent Literature 1 is an ophthalmological treatment system that uses a slit-lamp microscope as a component, and while it enables specialized diagnosis, it also requires a highly skilled medical specialist to operate the system in real time. For this reason, it is difficult to say that this system is an inexpensive and easy way to receive examinations and guidance by medical specialists.

The present invention solves the above-mentioned problems, and provides an eye imaging device and a diagnostic support system that can easily and inexpensively support examinations and guidance by medical specialists.

Solution to Problem

According to one embodiment of the present invention, an eye imaging device is provided including a housing with an opening that can be in contact with a head of an observer, a first photographic optical system arranged in the housing and configured to image a left eyeball of the observer from a left side, a second photographic optical system arranged in the housing opposite to the first photographic optical system and configured to image a right eyeball of the observer from a right side, a third photographic optical system arranged slidable in the housing in a direction in which the first photographic optical system and the second photographic optical system face each other and configured to image the left eyeball and the right eyeball of the observer from a front, and a storage unit configured to store images captured by the first photographic optical system, the second photographic optical system, and the third photographic optical system.

Further, a plurality of third photographic optical systems may be arranged.

Further, the first photographic optical system, the second photographic optical system, and the third photographic optical system may capture moving images.

According to one embodiment of the present invention, a diagnostic support system is provided including the eye imaging device further including a communication unit configured to transmit the images, a server connected to the eye imaging device and configured to store the images, and a terminal configured to display the images.

The terminal may display a plurality of the images at the same time.

Advantageous Effects of Invention

According to the present invention, there is provided an eye imaging device and a diagnostic support system that can support examination and guidance by a medical specialist inexpensively and easily.

BRIEF DESCRIPTION OF DRAWINGS

FIG. 5 is a flow diagram showing a contact lens prescription procedure according to one embodiment of the present invention.

DESCRIPTION OF EMBODIMENTS

Figure 1:
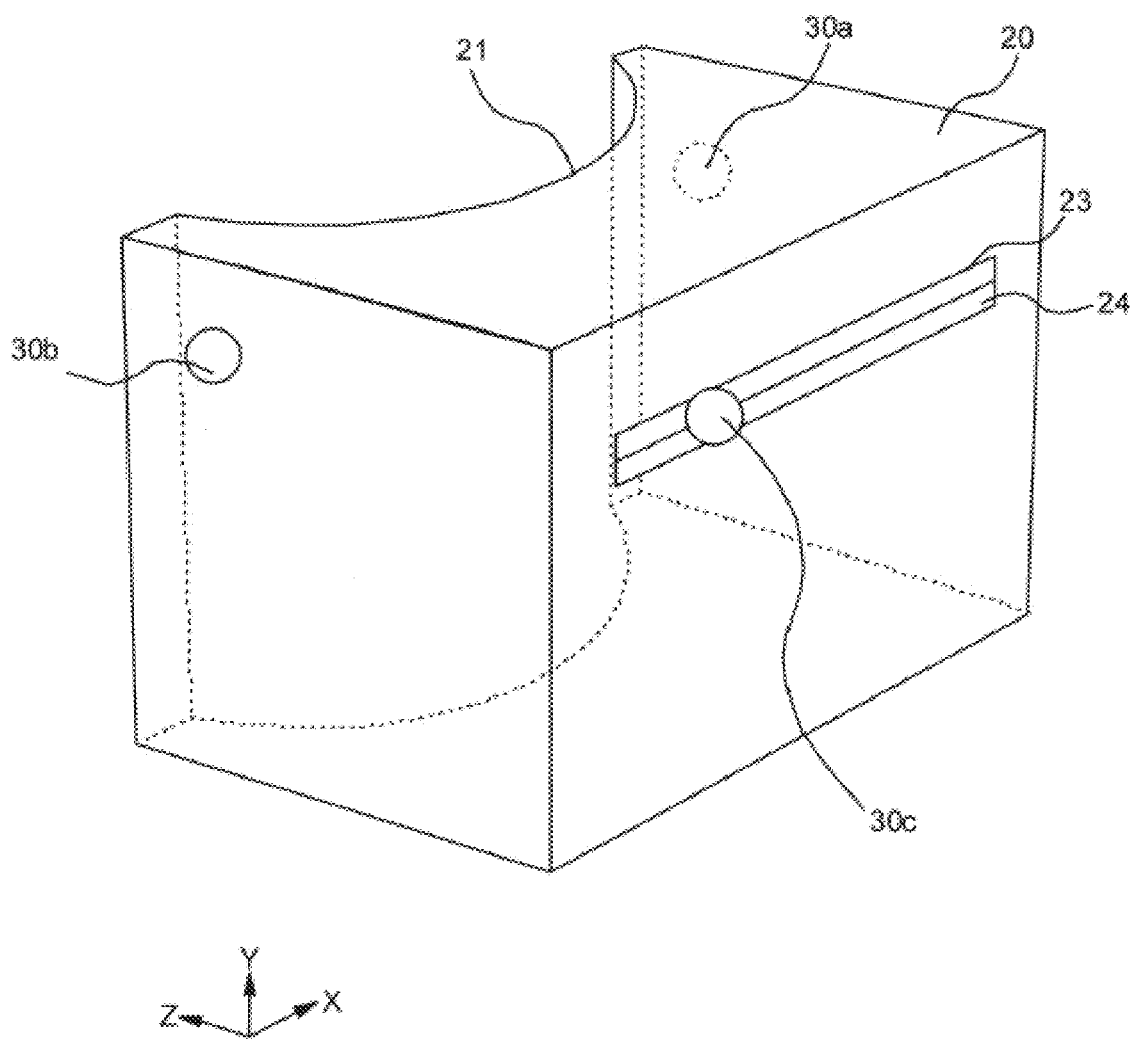
FIG. 1 is a schematic diagram of showing eye imaging device according to one embodiment of the present invention.

The eye imaging device according to the present invention is described below with reference to the drawings. The eye imaging device according to the present invention is not to be construed as limited to the description of the embodiment shown below. In the drawings referred to in this embodiment, the same sign is attached to the same part or the part having similar functions, and the repetition of the description is omitted.

<Eye Imaging Device>

FIG. 1 shows a schematic diagram of an eye imaging device according to one embodiment of the present invention. The eye imaging device 10 is a device capable of imaging the eyeball of an observer, and may be, for example, a box-shaped device as shown in FIG. 1. The eye imaging device 10 may be a device that can be worn on the head of the observer, and may further be a goggle-type device having a band as a fixing means.

The eye imaging device 10 has a housing 20, a first camera 30a (first photographic optical system) that images the left eyeball of the observer from the side, a second camera 30b (second photographic optical system) that images the right eyeball of the observer from the side, and a third camera 30c (third photographic optical system) that images the left and right eyeballs of the observer from the front (third photographic optics). Here, the first camera 30a, the second camera 30b, and the third camera 30c are referred to as camera 30 when they are not distinguished.

The housing 20 has an opening 21 that can contact with the head (face) of the observer. In one embodiment, the opening 21 is shown as a semi-cylindrical hollowed-out shape of the housing 20 so as to correspond to the curved surface of the upper part of the face of the observer. In other words, the housing 20 has the opening 21 in a curved concave part. However, it is not limited to this, and the opening 21 should be able to image the observer's eyes from the front and side when the housing 20 is in contact with the observer's head. For example, the housing 20 itself may be curved so as to correspond to the curved surface of the upper part of the observer's face. The housing 20 is preferably made of light-shielding material to suppress the influence of light from the environment in which the eye imaging device 100 is used. The edge of the opening 21 is preferably made of a flexible material to accommodate various head shapes of the observer. The housing has a slit 23 on the opposite (front) side of the opening 21. The slit 23 is located at the height corresponding to the eyeball (Y direction) when the housing 20 is in contact with the head (face) of the observer, and extends in the direction corresponding to the left eyeball and the right eyeball (X direction). A light-shielding valve 24 is arranged at the edge of the slit 23 to prevent light from leaking through. The light-shielding valve 24 is preferably made of a flexible material to prevent light from leaking even when the third camera 30c (described below) is arranged. If the housing 20 is light-shielding, the housing 20 preferably further have a light source. The light source is preferably located inside the housing 20. Arranging the light source inside the housing 20 allows for clearer imaging of the observer's eye. However, it is not limited to this, for example, the housing 20 may be transparent only on the upper side. By configuring the housing 20 in this way, the same effect as arranging the light source on the upper side can be obtained.

In one embodiment, the camera 30 is a photographic optical system that captures images of the eyes of the observer 1, and may include a single focal length lens, or may include a zoom lens.

In one embodiment, the first camera 30a is arranged at the position of the housing 20 that can image the left eyeball of the observer from the left side in the reverse X direction. The second camera 30b is arranged at the position of the housing 20 that can image the right eyeball of the observer from the right side in the X direction. In other words, in FIG. 1, the first camera 30a is arranged on the right side surface (X side surface) of the housing 20 and the second camera 30b is arranged on the left side surface (reverse X side surface) of the housing 20. The first camera 30a and the second camera 30b are opposite each other. The third camera 30c is arranged at the position of the housing 20 that can image the left eyeball and the right eyeball of the observer from the front in the Z direction. In other words, in FIG. 1, the third camera 30c is arranged at the front surface (opposite Z side surface) of the housing 20. The third camera 30c is placed at the slit 23 of the housing 20. The third camera 30c is positioned in the slit 23 so that it can slide in the direction (X direction) where the first camera 30a and the second camera 30b face each other. In other words, the third camera 30c can move to the position of the housing 20 that can image the observer's left eyeball from the front in the z direction, and can also move to the position that can image the observer's right eyeball from the front in the z direction. The first camera 30a, the second camera 30b, and the third camera 30c are all arranged at a height (in the Y direction) corresponding to the eyeball when the housing 20 is in contact with the observer's head (face).

In one embodiment, the eye imaging device 10 has one first camera 30a, one second camera 30b, and one third camera 30c. However, this is not limited, and the first camera 30a, the second camera 30b, and the third camera 30c may all be arranged in plural numbers. For example, the first camera 30a and the second camera 30b may be plural in the Y-Z direction and the third camera 30c may be plural in the X-Y direction so as to correspond to various eye positions of the observer.

Figure 2:
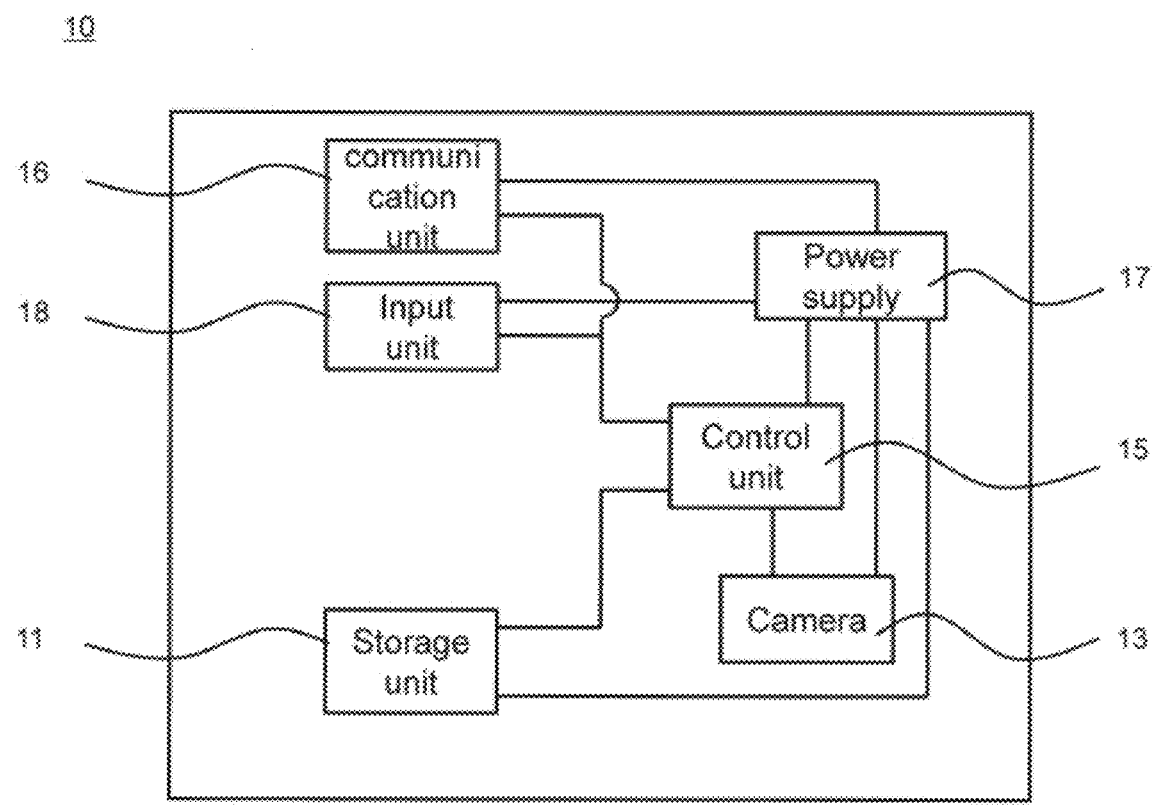
FIG. 2 is a block configuration diagram showing the eye imaging device according to one embodiment of the present invention.

FIG. 2 is a block configuration diagram of an eye imaging device according to one embodiment of the present invention. The eye imaging device include, for example, but not limited to, a camera 30, a storage unit 11, a control unit 15, a communication unit 16, a power supply 17, and an input unit 18.

The storage unit 11 is, for example, a memory and may temporarily store images of the observer's eyes captured by the camera 30. The storage unit 11 may store the authentication information of the observer together with the image of the observer's eyeball captured by the camera 30. In one embodiment, the observer can be identified based on the authentication information. The memory may include a recording medium that can be read by a computer, such as a memory card.

The control unit 15 is a device that controls the eye imaging device 10, and is, for example, a central processing unit (CPU). The control unit 15 includes a program to control the eye imaging device 10. The program to control the eye imaging device 10 is stored in the storage unit 11 and executed by the control unit 15. In addition, in one embodiment, the control unit 15 may include an operating system (OS) that controls the eye imaging device 10.

The communication unit 16 is a device that communicates between the eye imaging device 10 and the external devices. For example, it includes a communication means that conforms to the wireless communication standards such as, but not limited to, Wi-Fi (registered trademark) (a communication means that uses the IEEE 802.11 standard) or Bluetooth (registered trademark). A physical address (MAC address) is assigned to the communication unit 16, and the eye imaging device 10 can be identified from the physical address. In other words, the physical address (MAC address) assigned to the communication unit 16 may be used as the terminal identification information of the eye imaging device 10. The physical address of the eye imaging device 10 is, for example, associated with a contact lens sales store. Therefore, the contact lens sales store can be identified based on the physical address of the eye imaging device 10. In one embodiment, the eye imaging device 10 may be connected to the diagnostic support system via wireless communication by the communication unit 16 and transmit the image of the eyeball of the observer captured by the camera 30. The eye imaging device 10 may transmit the authentication information of the observer to the diagnostic support system together with the image of the observer's eyeball captured by the camera 30. As described below, the eye imaging device 10 may also be connected to a terminal for a medical worker 131 via wireless communication by the communication unit 16.

The power supply 17 is a general battery that can be repeatedly charged and discharged to supply power to each device installed in the eye imaging device 10. For example, the power supply 17 includes a connection terminal and may be charged by an external power supply. The power supply 17 may also be charged by wireless power transmission by supplying power from the outside without contact. The power supply 17 is preferably lightweight and have a large capacity, but it is not limited. Therefore, the eye imaging device 10 is not limited to use only within the contact lens stores, but can be portable.

The input part 18 is an input means by which the observer 1 can operate the eye imaging device 10. For example, it may be a switch, a selection button, a touch panel, or the like. In one embodiment, the input part 18 may be a display device (e.g., liquid crystal display or organic EL display) included with a touch panel. The shape and position of the input part 18 can be selected arbitrarily and is not limited. Input part 18 may, for example, be operated by the observer 1 pressing the button to start imaging the eyeball. When the input part 18 includes a display device, for example, the image of the observer 1's eyeball captured by the camera 30 may be displayed on the display device and used to align the eyeball with the camera.

In one embodiment, the authentication information of the observer 1 is the name, authentication code, etc. of the observer 1, and can be any information that identifies the observer 1. It is also preferable that the authentication information of the observer 1 includes, for example, a code indicating that the observer 1 has a past history.

By having such a configuration, the eye imaging device 10 of this embodiment can inexpensively and easily capture frontal and lateral images of the eyeballs of the observer 1, and can support examination and guidance by medical specialists.

<Diagnostic Support System>

Figure 3:
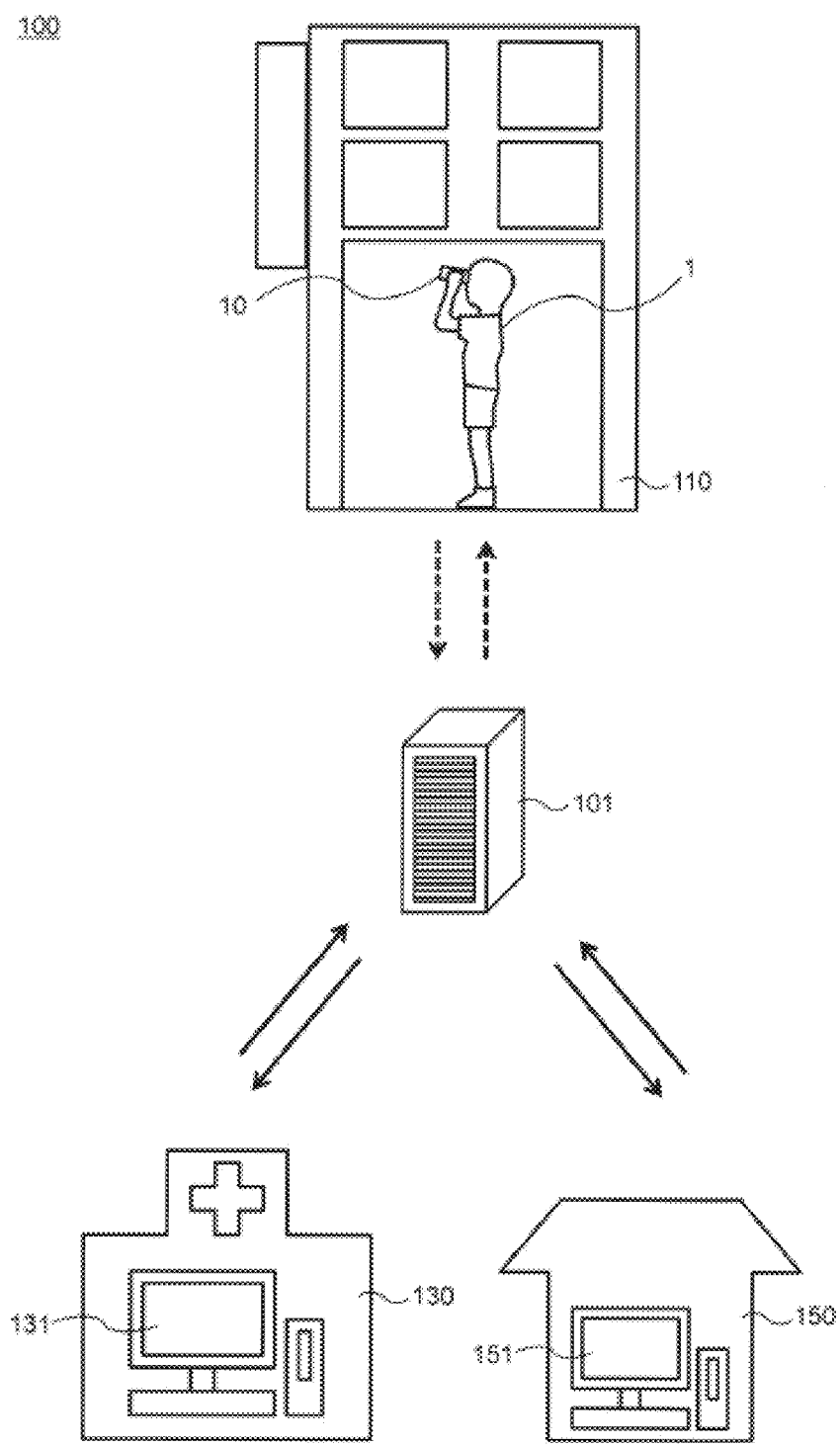
FIG. 3 is a schematic diagram showing a diagnostic support system according to one embodiment of the present invention.

FIG. 3 shows a schematic diagram of a diagnostic support system 100 according to one embodiment of the present invention. The diagnostic support system 100 comprises, for example, but is not limited to, an eye imaging device 10, a server 101, and terminals for the medical workers 131 and 151. The server 101 is, for example, a server that can be connected via wireless communication with the eye imaging device 10, and is connected via wired or wireless communication with the terminals for medical workers 131 and 151 at the medical institution 130 or the medical worker's home 150. In other words, the server 101 is a server that functions as a hub to connect the eye imaging device 10 to the terminals for the medical workers 131 and 151 in the diagnostic support system 100. The hardware of the server 101 is not particularly limited and comprises a known server and various electronic devices included in the known server.

In one embodiment, the server 101 may store the information of the observer 1 and the terminal specific information of the eye imager 10 in association with the image of the eyeball of the observer 1 captured by the eye imaging device 10. The information of the observer 1 is the name, address, medical history, etc. of the observer 1, and can be any information that identifies the observer 1. The information of the observer 1 may preferably include, for example, the radius of curvature of the cornea, the diameter of the cornea, and the naked eye visual acuity of the observer 1. The information of the observer 1 may also include the information of the contact lenses used or being used by the observer 1.

In one embodiment, it is preferable that the storage area for storing the information of the observer 1 in the server 101 is stored in an area that can be accessed only by experts such as medical professionals. The terminals for medical workers 131 and 151 can write the information of the observer 1 by connecting to the server 101. Therefore, in this embodiment, the information of the observer 1 can be rewritten only by those who can operate the terminals for medical workers 131 and 151, that is, experts such as medical worker.

The terminals for medical workers 131 and 151 include wireless communication means and may communicate with the server 101 of the diagnostic support system 100 via wireless communication. For this purpose, the terminal for medical workers 131 and 151 may be a tablet-type terminal such as a cell phone, smart phone, or iPad (registered trademark) owned by the medical workers.

The medical institution 130 includes a medical institution with at least an ophthalmologist. The medical institution 130 also includes a contact lens specialty store with an ophthalmologist. The medical institution 130 includes a terminal for medical workers 131 and is connected to the server 131 via wired or wireless communication. Therefore, the terminal for medical workers 131 can be connected to the diagnostic support system 100 via the server 101. The terminal for medical workers 131 can be a general-purpose computer terminal or a dedicated terminal. For example, a personal computer, a tablet-type terminal such as iPad (registered trademark), a smartphone, or any other terminal that can receive e-mails can be used as the terminal for medical workers 131. In one embodiment, the terminal for medical workers 131 may be connected to the diagnostic support system 100 without going through the server 101. The terminal for medical workers 131 may receive the image of the eyeball of the observer 1 from the diagnostic support system 100 and enable the medical worker to monitor the condition of the eye of the observer 1. In addition, when an abnormality is detected in the condition of the eye of the observer 1, the terminal for medical worker 131 may notify the diagnostic support system 100 of the abnormality. When the terminal for medical workers 131 notifies the diagnostic support system 100 of an abnormality in the eye condition of the observer 1, the contact lens sales store 110 preferably notifies the observer 1 of the result of the examination.

Also, in one embodiment, the terminal for medical workers 151 for may be installed at the home 150 of the medical worker. The priority of the terminal for the medical worker 131 to be notified of the acquisition of the image of the eyeball of the observer 1 from the diagnostic support system 10 may be registered in the server 101. The server 101 notifies terminal for the medical worker 131 having the first priority (e.g., a family ophthalmologist) of the acquisition of the image of the eyeball of the observer 1. If there is no response from the first terminal for the medical worker 131, the server 101 may notifies the second terminal for the medical worker 131 (e.g., an ophthalmologist) of the acquisition of the image of the eyeball of the observer 1. Also, in one embodiment, if there is no response from the first terminal for the medical worker 131, the server 101 may notifies the terminal for the medical worker 151 at the medical worker's home 150 of the acquisition of the image of the eyeball of the observer 1. In one embodiment, the image of the eyeball of the observer 1 may be stored in the server 101, and then the terminals for the medical worker 131 and 151 who accessed the diagnostic support system 100 for the first time may be notified of the acquisition of the image of the eyeball of the observer 1. The terminal for the medical worker 131 and 151 display an image of the eyeball of the observer 1 provided by the server 101, by storing in its storage device and execute an application capable of displaying the image of the observer 1's eyeball obtained from the diagnostic support system 100, or by the server 100 via an Internet browser.

Figure 4:
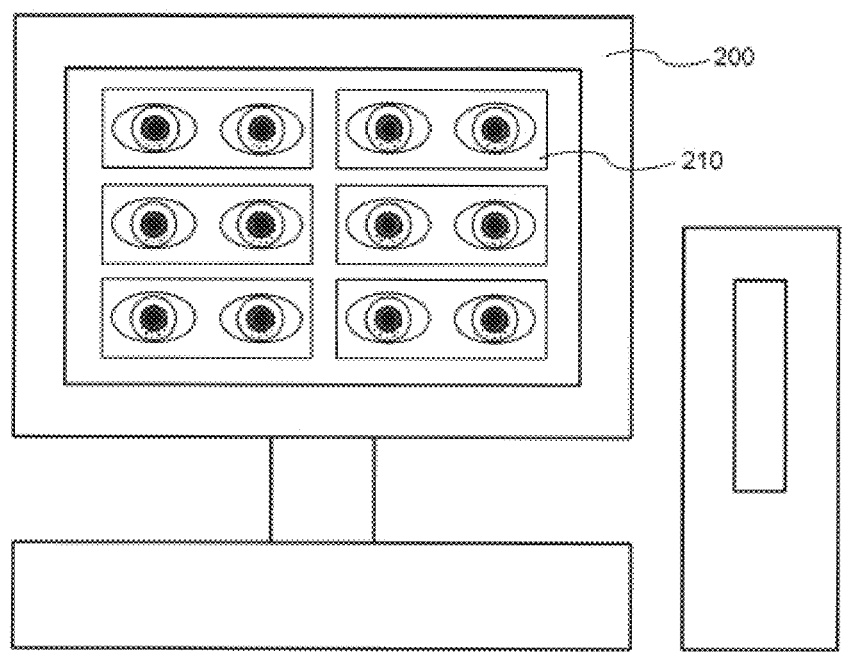
FIG. 4 is a schematic diagram showing a diagnostic support display screen according to one embodiment of the present invention.

FIG. 4 is a schematic diagram showing a diagnostic support display screen 200 according to one embodiment of the present invention. For example, in FIG. 4, the diagnostic support display screen 200 shows frontal images 210 of the eyeballs of six observers) obtained from the diagnostic support system 100 on the display of the terminal for the medical worker 131, but this is not limited to this. For example, the frontal and left side and right side images of the eyeballs of one or more observer 1 may be displayed simultaneously. The frontal and left and right lateral images of the observer's eye may be displayed as 3D images. The images 210 of the eyeballs of the examinee 1 may be displayed as the moving images or still images, respectively. The moving images 210 of the eyes of multiple observers 1 may be played back simultaneously, or they may be played back for one person at a time.

Also, in one embodiment, the images of the eyeballs of the observer 1 obtained from the diagnostic support system 100 may be stored in the server 101. An expert such as medical worker may simultaneously view the images of the eyeballs of the observer 1 stored and accumulated in the server 101 via the terminal for the medical worker 131. The medical worker can use the changes over time for diagnosis based on the results of the examinations of the observer 1 and the stored images of the eyeballs of the observer 1 at the time of the periodic examinations of the observer 1. For this purpose, an expert such as medical worker may periodically update the examinations information by storing the examinations results in the server 101 via the terminal for the medical worker 131.

With this configuration, the diagnostic support system 100 according to the present embodiment can inexpensively and easily capture frontal and lateral images of the eyeballs of the observer 10 and support examination and guidance by medical specialists. Since the location and time of the observer and medical worker are not limited, the system can efficiently support examinations and guidance by medical specialists.

<Contact Lenses Prescription Procedure>

FIG. 5 is a flow diagram explaining the contact lenses prescription procedure according to one embodiment of the present invention. First, a medical interview (1) is conducted with the person who wants the contact lenses prescription. In the interview, the eye condition, living conditions, and contact lenses usage status and the like of the person who wants the contact lenses prescription are inquired.

Next, an anterior segment of the eye examination (2) is performed using the eye imaging device 10 of the present embodiment. The frontal and lateral images of the left and right naked eyes of the person who wants the contact lenses prescription (observer 1) are captured using the eye imaging device 10. The images of the observer's eyeballs are monitored by a medical specialist in real time or by recording via the diagnostic support system 100. In the anterior segment of the eye examination, the observer 1's eye is observed for abnormalities such as cloudy lens, hyperemia of the conjunctiva, and inflammation.

Figure 6:
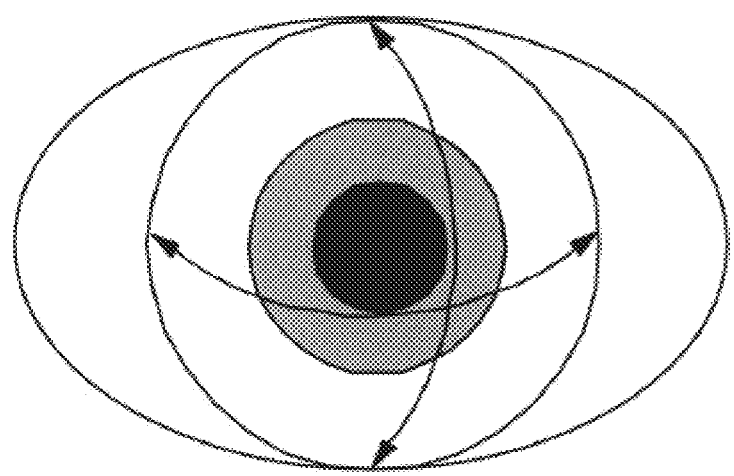
FIG. 6 is a schematic diagram showing a method of measuring corneal radius of curvature and corneal diameter according to one embodiment of the present invention.

If there is no abnormality in the condition of the observer's eye, the next step is the measurement of the radius of curvature of the cornea (3), the measurement of the diameter of the cornea (4), the measurement of the naked eye visual acuity (5), the refraction test (6), and the tear fluid volume test (7) using an autorefractometer. FIG. 6 is a schematic diagram illustrating the method of measuring corneal radius of curvature and corneal diameter. As shown in FIG. 6, in the measurement of corneal radius of curvature (3) and corneal diameter (4), the values of the vertical curve and horizontal curve of the cornea and the corneal diameter are measured. Select a trial lens based on the intermediate values of the vertical curve and horizontal curve of the corneal and the corneal diameter (8), and wear the trial lens (9).

Next, a contact lens fitting inspection (10) is performed using the eye imaging device 10 of the present embodiment. The frontal and lateral images of the left and right naked eyes when wearing contact lenses are captured in moving images using the eye imaging device 10. The images of the eyeballs of the observer 1 wearing contact lenses are monitored by a medical worker in real time or in recording via the diagnostic support system 100. During the contact lens fitting inspection, the movement of the contact lens on the eyeball is observed.

Figure 7A:
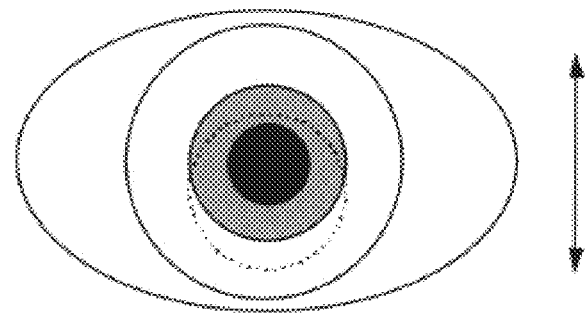
FIG. 7A is a schematic diagram showing the fitting state of a contact lens according to one embodiment of the present invention.
Figure 7B:
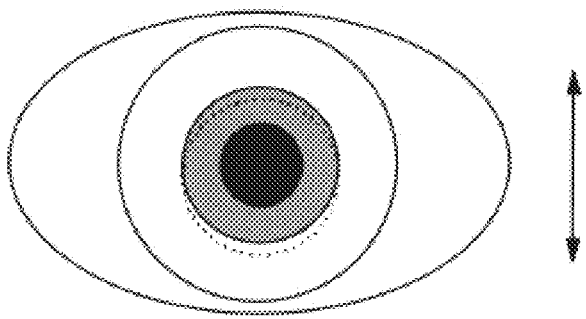
FIG. 7B is a schematic diagram showing the fitting state of a contact lens according to one embodiment of the present invention.
Figure 7C:
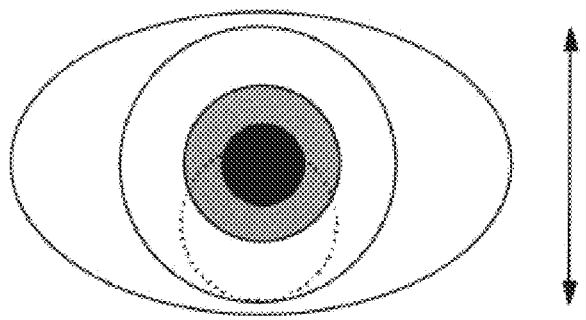
FIG. 7C is a schematic diagram showing the fitting state of a contact lens according to one embodiment of the present invention.
Figure 8A:
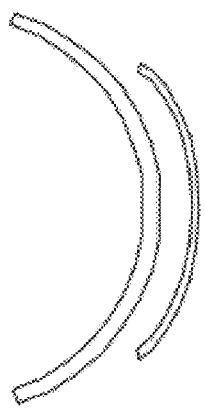
FIG. 8A is a schematic diagram showing the movement of a contact lens in an image according to one embodiment of the present invention.
Figure 8B:
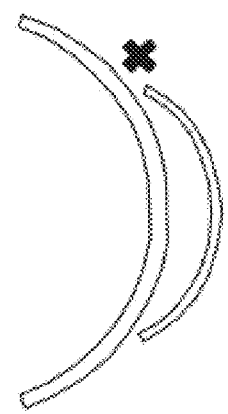
FIG. 8B is a schematic diagram showing the movement of a contact lens in an image according to one embodiment of the present invention.
Figure 8C:
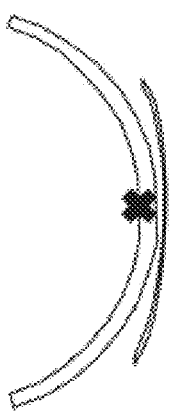
FIG. 8C is a schematic diagram showing the movement of a contact lens in an image according to one embodiment of the present invention.

FIGS. 7A-7C are the schematic diagrams showing the fitting of a contact lens according to one embodiment of the present invention. FIGS. 8A-8C are the schematic diagrams showing the movement of a contact lens in an image according to one embodiment of the present invention. As shown in FIG. 7A, when the fitting of the contact lens is normal, the corneal curve and the contact lens curve are substantially parallel, and the contact lens floats on the cornea with tears sandwiched between them. For this reason, as shown in FIG. 8A, the contact lens is lifted by the eyelids with each blink, and then falls slowly by gravity.

As shown in FIG. 7B, if the radius of curvature of the contact lens is smaller than the radius of curvature of the cornea, the curve of the contact lens is tighter than the curve of the cornea, and the edge (outer circumference) of the contact lens touches the eyeball. For this reason, the contact lens tends to adhere to the eyeball, and as shown in FIG. 8B, the movement of the contact lens on the eyeball becomes small and slow.

When the radius of curvature of the contact lens is larger than the radius of curvature of the cornea, as shown in FIG. 7C, the curve of the contact lens is gentler than the curve of the cornea, and the center of the contact lens touches the eyeball. For this reason, the contact lens tends to float from the eyeball, and the movement of the contact lens on the eyeball becomes larger and faster, as shown in FIG. 8C.

The fitting of the contact lenses may be judged by the width of the movement of the contact lenses as described above, or by the speed of the movement of the contact lenses.

In one embodiment, the fitting of the contact lens may be determined by a fluorescein pattern. Tear fluid is dyed with fluorescein, and the frontal and lateral images of the left and right naked eyes when wearing contact lenses are captured using an eye imaging device 10. In this case, it is preferable to use a blue light as the light source. The images of the eyeballs of the observer 1 wearing contact lenses are monitored by a medical specialist in real time or by recording via the diagnostic support system 100. The contact lens fitting inspection with fluorescein pattern observes the placement of the tear fluid layer between the cornea and the lens.

Figure 9A:
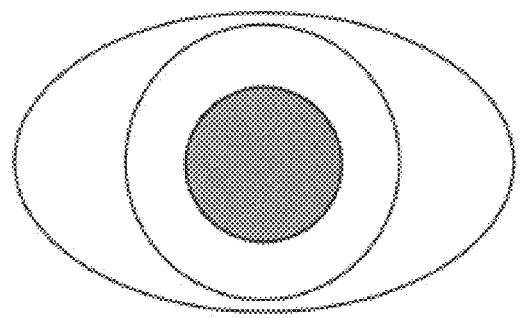
FIG. 9A is a schematic diagram showing fluorescein pattern in an image according to one embodiment of the present invention.
Figure 9B:
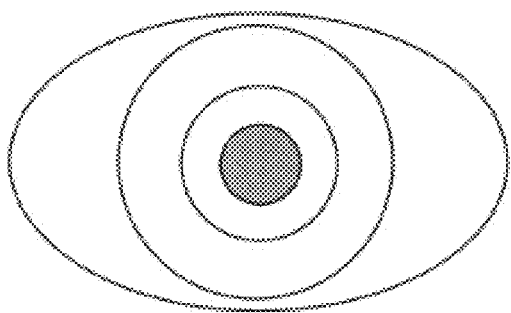
FIG. 9B is a schematic diagram showing fluorescein pattern in an image according to one embodiment of the present invention.
Figure 9C:
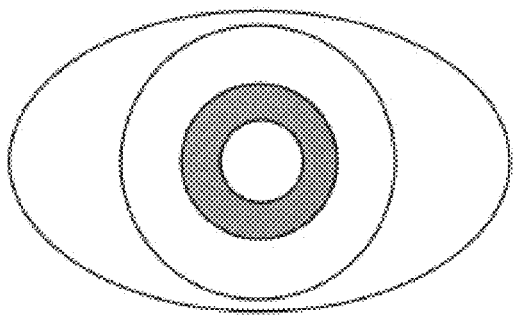
FIG. 9C is a schematic diagram showing fluorescein pattern in an image according to one embodiment of the present invention.

FIGS. 9A-9C are the schematic diagrams showing fluorescein pattern in an image according to one embodiment of the present invention. When the fitting of the contact lens is normal, the corneal curve and the contact lens curve are roughly parallel, and the contact lens floats on the cornea across the tears. For this reason, the space between the cornea and the contact lens is evenly stained with fluorescein, as shown in FIG. 9A.

If the radius of curvature of the contact lens is smaller than the radius of curvature of the cornea, the curve of the contact lens will be tighter than the curve of the cornea, and the edge (outer periphery) of the contact lens touches the eyeball. For this reason, the space between the cornea and the contact lens is stained with fluorescein in the center, as shown in FIG. 9B.

If the radius of curvature of the contact lens is larger than the radius of curvature of the cornea, the curve of the contact lens is gentler than the curve of the cornea, and the center of the contact lens touches the eyeball. For this reason, the space between the cornea and the contact lens is stained with fluorescein at the periphery, as shown in FIG. 9C.

If there is no abnormality in the fitting of the contact lens, the next step is to perform a forced vision test (11) and determine the lens standard (12). Finally, guidance on the appropriate handling for the determined lens is given (13).

The diagnostic support system 100 according to one embodiment can support anterior segment of the eye examinations (2) and fitting inspection (10) by medical specialists regarding contact lens prescription. Since it does not select the location or time of the observer or medical specialists, it can efficiently support the examination and guidance by the medical specialist.

EXAMPLES

As a group I, the fitting inspection of trial lenses at the time of the initial orthokeratology prescription was performed on six observers using the eye imaging device 10 of the present embodiment. In subsequent periodic examinations, anterior segment of the eye examinations were performed with the naked eye using the eye imaging device 10 of this embodiment. In both the fitting and anterior segment of the eye examinations, a face-to-face follow-up examination was conducted by a medical specialist. As a result, it was confirmed that the examination using the eye imaging device 10 of the present embodiment provided results equivalent to those obtained by face-to-face examination using a slit-lamp microscope or the like. In addition, no adverse events such as contact dermatitis, corneal damage, or damage due to phototoxicity were observed in the observer by the examination using the eye imaging system 10. Therefore, it can be seen that the examination using the eye imaging device 10 in this study is useful at the time of orthokeratology prescription and in subsequent periodic examinations, except when special examinations such as tear fluid volume test or corneal shape measurement are required.

As a group II, five observers with allergic conjunctivitis and suspected VDT (visual display terminal) syndrome underwent anterior segment of the eye examination using the eye imaging device 10 of the present embodiment. In each of the anterior segment of the eye examinations, a face-to-face follow-up examination was conducted by a medical specialist. As a result, it was confirmed that the examination using the eye imaging device 10 of the present embodiment can provide useful examination information for the diagnosis of the same disease, and that the results are equivalent to those obtained by face-to-face examination using a slit-lamp microscope. In addition, no adverse events such as contact dermatitis, corneal damage, or damage due to phototoxicity were observed in the observer as a result of the examination using the eye imaging device 10 of the present embodiment. Therefore, it can be seen that the examination using the eye imaging device 10 of the present embodiment is useful in the diagnosis of allergic conjunctivitis, suspected cases of VDT syndrome, etc., except when a special examination is required.

REFERENCES SIGNS LIST

1: observer, 10: Eye imaging device, 100: Diagnostic support system, 101: Server, 131,135 Terminal for medical worker

The invention claimed is:

1. An eye imaging device comprising:
 a housing with an opening that can be in contact with a head of an observer;
 a first photographic optical system arranged in the housing and configured to image a left eyeball of the observer from a left side;
 a second photographic optical system arranged in the housing opposite to the first photographic optical system and configured to image a right eyeball of the observer from a right side;
 a third photographic optical system arranged slidable in the housing in a direction in which the first photographic optical system and the second photographic optical system face each other and configured to image the left eyeball and the right eyeball of the observer from a front; and
 a storage unit configured to store images captured by the first photographic optical system, the second photographic optical system, and the third photographic optical system.

2. The eye imaging device according to claim 1, wherein there are a plurality of the third photographic optical systems.

3. The eye imaging device according to claim 1, wherein the first photographic optical system, the second photographic optical system, and the third photographic optical system capture moving images.

4. The eye imaging device according to claim 2, wherein the first photographic optical system, the second photographic optical system, and the third photographic optical system capture moving images.

5. A diagnostic support system comprising:
 an eye imaging device comprising:
  a housing with an opening that can be in contact with a head of an observer;
  a first photographic optical system arranged in the housing and configured to image a left eyeball of the observer from a left side;
  a second photographic optical system arranged in the housing opposite to the first photographic optical system and configured to image a right eyeball of the observer from a right side;
  a third photographic optical system arranged slidable in the housing in a direction in which the first photographic optical system and the second photographic optical system face each other and configured to image the left eyeball and the right eyeball of the observer from a front;
  a storage unit configured to store images captured by the first photographic optical system, the second photographic optical system, and the third photographic optical system; and
  a communication unit configured to transmit the images;
 a server connected to the eye imaging device and configured to store the images; and
 a terminal configured to display the images.

6. The diagnostic support system according to claim 5, wherein there are a plurality of the third photographic optical systems.

7. The eye imaging device according to claim 5, wherein the first photographic optical system, the second photographic optical system, and the third photographic optical system capture moving images.

8. The eye imaging device according to claim 6, wherein the first photographic optical system, the second photographic optical system, and the third photographic optical system capture moving images.

9. The diagnostic support system according to claim 5, wherein the terminal displays a plurality of the images at the same time.

10. The diagnostic support system according to claim 6, wherein the terminal displays a plurality of the images at the same time.

11. The diagnostic support system according to claim 7, wherein the terminal displays a plurality of the images at the same time.

12. The diagnostic support system according to claim 8, wherein the terminal displays a plurality of the images at the same time.

* * * * *